(12) United States Patent
Touitou et al.

(10) Patent No.: US 7,736,630 B2
(45) Date of Patent: Jun. 15, 2010

(54) PRODUCTS FOR PREVENTING PENETRATION INTO THE SKIN

(76) Inventors: Elka Touitou, 6 Demumit Street, Givat Canada, Jerusalem 93893 (IL); Lev Bergelson, 59 HaShofar Street, Maaleh Adumim 98330 (IL)

( * ) Notice: Subject to any disclaimer, the term of this patent is extended or adjusted under 35 U.S.C. 154(b) by 1777 days.

(21) Appl. No.: 10/473,358

(22) PCT Filed: Mar. 26, 2002

(86) PCT No.: PCT/IL02/00254

§ 371 (c)(1), (2), (4) Date: May 3, 2004

(87) PCT Pub. No.: WO02/079121

PCT Pub. Date: Oct. 10, 2002

(65) Prior Publication Data

US 2004/0208904 A1    Oct. 21, 2004

(51) Int. Cl.
*A61K 8/00* (2006.01)
*A61K 8/18* (2006.01)
*A61Q 17/04* (2006.01)

(52) U.S. Cl. .......................... 424/59; 424/60

(58) Field of Classification Search .................... 424/59, 424/60
See application file for complete search history.

(56) References Cited

U.S. PATENT DOCUMENTS

| | | | |
|---|---|---|---|
| 4,749,517 A | 6/1988 | Chwang et al. | |
| 5,243,064 A | 9/1993 | Sabatelli et al. | |
| 5,547,659 A | 8/1996 | Rinaldi et al. | |
| 5,676,994 A | 10/1997 | Eskins et al. | |
| 5,814,310 A * | 9/1998 | Nagy et al. | 424/65 |
| 5,882,713 A | 3/1999 | Eskins et al. | |
| 5,925,364 A | 7/1999 | Ribier et al. | |
| 2004/0208904 A1 | 10/2004 | Touitou | |

FOREIGN PATENT DOCUMENTS

| | | | |
|---|---|---|---|
| JP | 61 210054 | | 9/1986 |
| JP | 6120054 | * | 9/1986 |

OTHER PUBLICATIONS

Supplementary European Search Report for EP 02 72 2641 dated Nov. 8, 2005.
Committee on Jojoba Utilization, Office of Chemistry and Chemical Technology, Assembly of Mathematical and Physical Sciences, National Research Council, "Products from Jojoba: A Promising New Crop for Arid Lands", National Academy of Sciences, Washington, DC, 1975.
Johnson et al . "Oils and Rubber from Arid Land Plants", Science, vol. 208, 1980. pp. 460-464.
Arnon Shani, "Functionalization at the Double-Bond Region of Jojoba Oil 3. Hydroxylic Derivatives". Ind Eng. Chem Prod Res Dev. . 1983, 22, pp. 121-123.
Arnon Shani. "Functionalization at the Double-Bond Region of Jojoba Wax 4 *all-trans*-Jojoba Wax and Its Derivatives", Ind Eng Chem. Prod. Res Dev , 1986. 25, pp. 78-82.
Hampel and Hawley, Eds . The Encyclopedia of Chemistry. Third Edition, Van Nostrand Reinhold Company, 1973. pp. 632.
International Search Report for PCT/IL02/00254 dated Dec. 9, 2003.

* cited by examiner

*Primary Examiner*—Johann R Richter
*Assistant Examiner*—Kristie L Brooks
(74) *Attorney, Agent, or Firm*—The Nath Law Group; Susanne M. Hopkins; Ari G. Zytcer

(57) ABSTRACT

The present invention relates to novel cosmetic and/or dermatological compounds and compositions for the photoprotection of human skin and/or hair against the damaging effects of UV radiation, in particular solar radiation. In another embodiment the invention relates to compositions and compounds for topical application comprising at least one photoprotective compound for topical application comprising of hydroxylated derivatives of natural Jojoba wax/oil or its synthetic substitute, esterified with carboxylic acids or aminoacids bearing UV-absorbing groups.

24 Claims, 4 Drawing Sheets

PRODUCTS FOR PREVENTING PENETRATION INTO THE SKIN

FIELD OF THE INVENTION

The present invention relates to novel cosmetic and/or dermatological compounds and compositions for the photoprotection of human skin and/or hair against the damaging effects of UV radiation, in particular solar radiation. In another embodiment, the invention relates to compositions and compounds for topical application comprising at least one photoprotective compound for topical application comprising of hydroxylated derivatives of natural Jojoba wax/oil or its synthetic substitute, esterified with carboxylic acids or aminoacids bearing UV-absorbing groups as well as of Jojoba esters obtained by transesterification of the said wax/oil with alcohols bearing one or several UV-absorbing groups.

BACKGROUND OF THE INVENTION

During the last two decades the problem of photoprotection of the skin has attracted increasing attention. It has become clear that exposure to sunlight may cause not only erythema photoallergy and photoagining of the skin but also can damage the cutaneous immune system and induce or increase the probability of malignant transformations. These dangers are probably reinforced by the lately observed decrease of stratospheric ozone levels causing an increase of UV radiation on the ground level. Because of these consideration as well as for commercial reasons the development and production of sunscreen formulations has become a field of ever increasing activity.

Many of the existing sunscreen formulations are based on the use of benzophenones and methoxycinnamic acid derivatives. Although these synthetic chemicals are effective UV-absorbers their protective action is relatively short. Being small organic molecules with molecular mass of <300 Da they partly penetrate into deeper regions of the epidermis where they may have adverse reactions such as suppressing the immune system of the skin. Some of them may have estrogenic effects.

These antisun or sunscreen compositions are commonly in the form of an emulsion of oil-in-water type (namely, a cosmetically acceptable support comprising a continuous aqueous dispersing phase and a discontinuous oily dispersed phase) which contains, in various concentrations, one or more conventional lipophilic and/or hydrophilic organic screening agents which are capable of selectively absorbing harmful UV radiation, these screening agents (and their amounts) being selected as a function of the desired protection factor (the protection factor (PF) being expressed mathematically by the ratio of the irradiation time required to reach the erythema-forming threshold with the UV screening agent to the time required to reach the erythema-forming threshold without UV screening agent).

Therefore, it will be highly advantageous to develop long-lasting nonpenetrating photoprotectors confined to the stratum corneum, based on natural products.

SUMMARY OF THE INVENTION

In one embodiment, the inventions relates to a photoprotective compound for topical application comprising of hydroxylated derivatives of natural Jojoba wax/oil or its synthetic substitute, esterified with carboxylic acids or aminoacids bearing UV-absorbing groups.

In another embodiment, the invention relates to a suntanning compound for topical application comprising of hydroxylated derivatives of natural Jojoba wax/oil or its synthetic substitute, esterified with carboxylic acids or aminoacids for suntanning.

In another embodiment, the invention relates to a compound represented by the general formula (I)

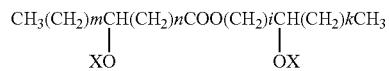

wherein X is an organic group absorbing light in the ultraviolet region or for suntanning and i, k, m, n are aliphatic chains containing from 5 to 30 methylene groups.

In another embodiment, the invention relates to a compound represented by the general formula (II)

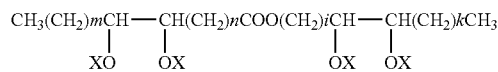

wherein X is an organic group absorbing light in the ultraviolet region or for suntanning and i, k, m, n are aliphatic chains containing from 5 to 30 methylene groups.

In another embodiment, the invention relates to a method of preparing di(4-methoxy cinnamoyl)jojobadiol comprising the step of esterification of jojobadiol with p-cinnamoyl chloride, thereby obtaining di(4-methoxy cinnamoyl)jojobadiol.

In another embodiment, the invention relates to a method of preparing tetra(4-methoxycinnamoyl)jojobatetraol comprising the step of esterification of jojobatetraol with p-cinnamoyl chloride, thereby obtaining tetra(4-methoxycinnamoyl)jojobatetraol.

In another embodiment the invention relates to derivatives of natural or hydrogenated Jojoba oil/wax obtained by trans esterification of the said oils/waxes with alcohols bearing an UV-absorbing group which are presented by the general formulae

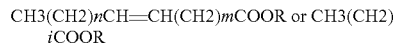

Where R is is an organic radical bearing a UV absorbing group.

DESCRIPTION OF THE DETAILED EMBODIMENTS

Figure 1:
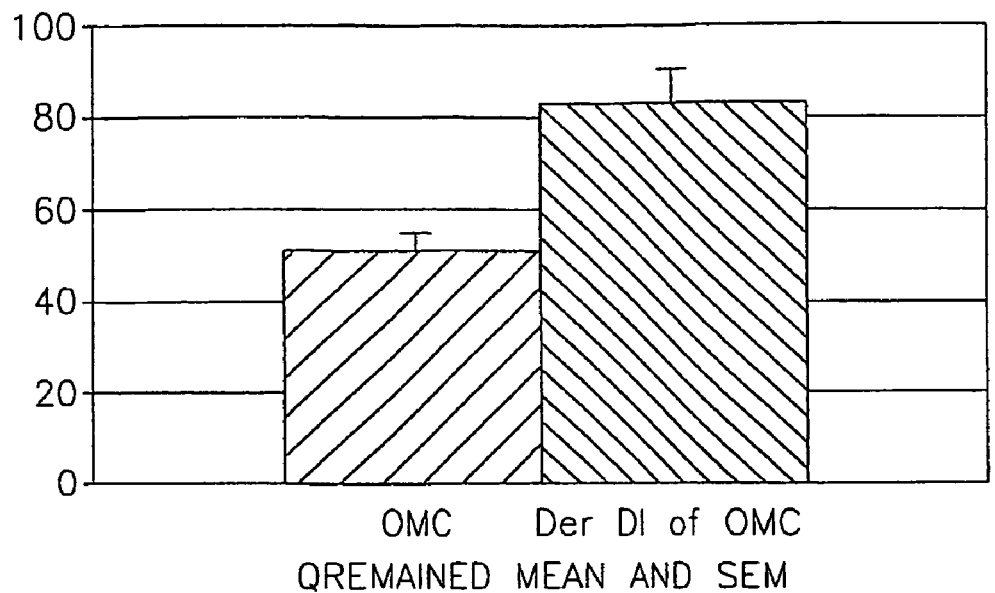
FIG. 1 presents the amount (in percents) of the OMC and di(4-methoxy cinnamoyl)jojobadiol, remained on the skin tissue after immersion in water and drying.
Figure 2:
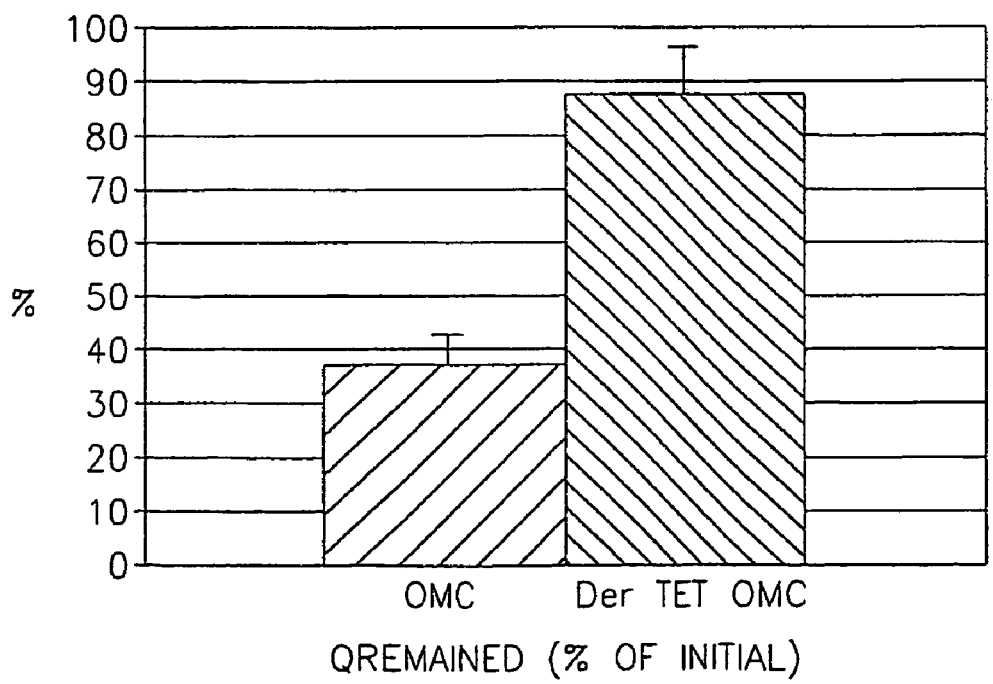
FIG. 2 presents the amount (in percents) of the OMC and tetra(4-methoxycinnamoyl)jojobatetraol, remained on the skin tissue after immersion in water and drying.

It is known to this art that light radiation having wavelengths of between 280 nm and 400 nm permits tanning of the human epidermis, and that light radiation having wavelengths of between 280 and 320 nm, known as UV-B irradiation, causes skin burns and erythema which may be harmful to the development of a natural tan; this UV-B radiation should therefore be screened from the skin. It is also known to this art that UV-A radiation, having wavelengths of between 320 nm and 400 nm, which causes tanning of the skin, is likely to induce an adverse change therein, especially in the case of sensitive skin or of skin which is continually exposed to solar radiation. UV-A radiation causes, in particular, a loss of elasticity of the skin and the appearance of wrinkles, resulting in premature skin aging. UV-A radiation promotes triggering of the erythemal reaction or amplifies this reaction in certain individuals and may even be the cause of phototoxic or photoallergic reactions. It is thus desirable to also screen UV-A radiation. Many cosmetic compositions suited for the photoprotection (UV-A and/or UV-B) of the skin are known to this art.

The present invention relates to the conversion of natural Jojoba wax/oil $CH_3(CH_2)_7CH=CH(CH_2)mCOO(CH_2)nCH=CH(CH_2)_7CH_3$ into light absorbing substances and their use as skin photoprotectors, by hydroxylating and further esterification with carboxylic acids or aminoacids bearing UV-absorbing groups or by transesterification of the said wax/oil or its hydrogenated derivatives with alcohols bearing UV-absorbing groups.

The term "esterification", or "esterified" refers hereinabove to a process on which carboxylic acids react with alcohols to yield a compound called ester.

By the term "oil" is intended a compound which is liquid at room temperature. By the term "wax" is intended a compound which is solid or more or semi solid or in another embodiment is liquid at room temperature.

The term "Jojoba wax/oil" includes also the derivatives or substituted compounds of Jojoba:

"Jojoba Oil" is a naturally golden liquid wax ester found in the seed of the jojoba plant. Jojoba oil is composed principally of 40 and 42 carbon chain esters, which are in turn composed of monounsaturated fatty acids and fatty alcohols of 20 and 22 carbon chain length. Jojoba oil contains less than 3% triglyceride and ist highly resistant to oxidation. The principal use of jojoba oil is for cosmetic purposes such as skin softening, skin penetration and emolliency.

"Hydrogenated Jojoba Oil" is a hard, crystalline wax ester created by the complete addition of hydrogen gas under pressure to all points of unsaturation within jojoba oil. The melting point of hydrogenated jojoba oil is 68-70° C. and the iodine value is <2.0 making it one of the most unique high melting wax esters of natural origin that is commercially available. Hydrogenated jojoba oil is relatively colorless, odorless and has particular functionality in cosmetic formulations such as lipstick, mascara, eyeliner, lip balm and similar formulas.

"Partially Hydrogenated Jojoba Oil" is a semi-soft to hard product resulting from the incomplete addition of hydrogen to points of unsaturation in jojoba oil. Partially hydrogenated jojoba oil is manufactured through a process known as "selective" or "controlled" hydrogenation or saturation. Partially hydrogenated jojoba oil (as with any partially hydrogenated vegetable oil) contains trans isomers, which have been shown to decrease normal skin metabolism.

"Jojoba Esters" is a complex mixture of esters produced by the transesterification of jojoba oil, hydrogenated jojoba oil, or a mixture of the tw with organic alcohols. Jojoba esters are produced in a broad range of melting points and are colorless, odorless and extremely resistant to oxidative degradation. Jojoba esters are useful as components of highly pigmented cosmetic systems.

Transisomerized Jojoba Oil Jojoba oil which has been subjected to the partial or complete transisomerization of its cis double bonds to form trans double bonds, and a higher melting, highly viscous product. This derivative of jojoba oil known as Jojoba butter or Jojobutter contains approximately 50% trans isomers.

In one embodiment, the inventions relates to a photoprotective compound for topical application comprising of hydroxylated derivatives of natural Jojoba wax/oil or its synthetic substitute, esterified with carboxylic acids or aminoacids bearing UV-absorbing groups. The term "photoprotective" refers hereinabove to a compound or a composition, which are applied to the skin so as to prevent the damages from the UV light.

In another embodiment, the invention relates to a suntanning compound for topical application comprising of hydroxylated derivatives of natural Jojoba wax/oil or its synthetic substitute, esterified with carboxylic acids or aminoacids for suntanning.

The term "suntanning compound" refers hereinabove to a compound which enhance the tanning, i.e the darkening of the color of the skin for example by exposure to the sun.

The term "topical application" relates hereinabove to application of substances to the skin or tissue by for example spreading them. Compositions for topical application are usually in a form of oily solutions, sticks, lotions, creams, suspensions, spray aerosols, films, microcapsules, microspheres, liposomes, vesicles, emulsions, microemulsions, lipospheres, patches, solutions, ethosomes, ethanolic solutions, alcoholic solutions.

The said substances were prepared by hydroxylation of the ethylenic bonds of Jojoba wax/oil and subsequent esterification with organic acids containing groups absorbing light in the UV region or by transesterification of natural or hydrogenated Jojoba wax/oil with alcohols containing UV-absorbing groups. Although derivatization of Jojoba wax/oil has been studied extensively in the past, (see "*Products from Jojoba: A Promising New Crop for Arid Lands*", Committee on Jojoba Utilization, Natl. Res. Council, 1975; Johnson, Hinman, Science 208, 460, 1980) only few attempts to hydroxylate the wax/oil have been reported.

In particular, no attempts to convert Jojoba wax/oil into dihydroxy derivatives (jojobadiols) are described in the literature, whereas jojobatetraols were prepared by epoxidation of natural Jojoba wax/oil with hydrogen peroxide in acetic acid in the presence of tetrabutylammonium bromide and subsequent hydrolytic cleavage of the diepoxide (Shani A., Ind. Eng. Chem. Prod. Res. Deve. 22, 121-123, 1983). A similar procedure involving epoxidation with m-chloroperbenzoic acid and subsequent cleavage of the diepoxide in boiling petroleum ether-20% HCl was used to tetrahydroxylate the unnatural trans-trans isomer of Jojoba wax/oil (Shani A. Ind. Eng. Chem. Prod. Res. Dev. 25, 78-82, 1986). However these procedures suffer from several shortcomings. In particular they are accompanied by formation of considerable amounts of undesired byproducts.

In another embodiment, the invention relates to a compound which resulted from the steps of hydroxylation followed by esterification which is represented by the general formula (I)

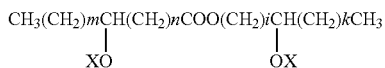

wherein X is an organic group absorbing light in the ultraviolet region or for suntanning and i, k, m, n are aliphatic chains containing from 5 to 30 methylene groups of the oily wax/oil esters isolated form the seeds of *Simmondsia chinensis* and *S. californica Nutt.* or *Buxaceae* desert shrubs below referred to as "Jojoba wax/oil".

In another embodiment, the invention relates to a compound represented by the general formula (II)

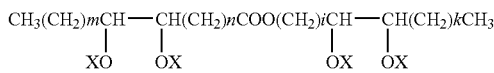

wherein X is an organic group absorbing light in the ultraviolet region or for, suntanning and i, k, m, n are aliphatic chains containing from 5 to 30 methylene groups.

In another embodiment the invention relates to compounds represented by the general formulae:

wherein R is the residue of an alcohol bearing an UV-absorbing group.

Figure 6:
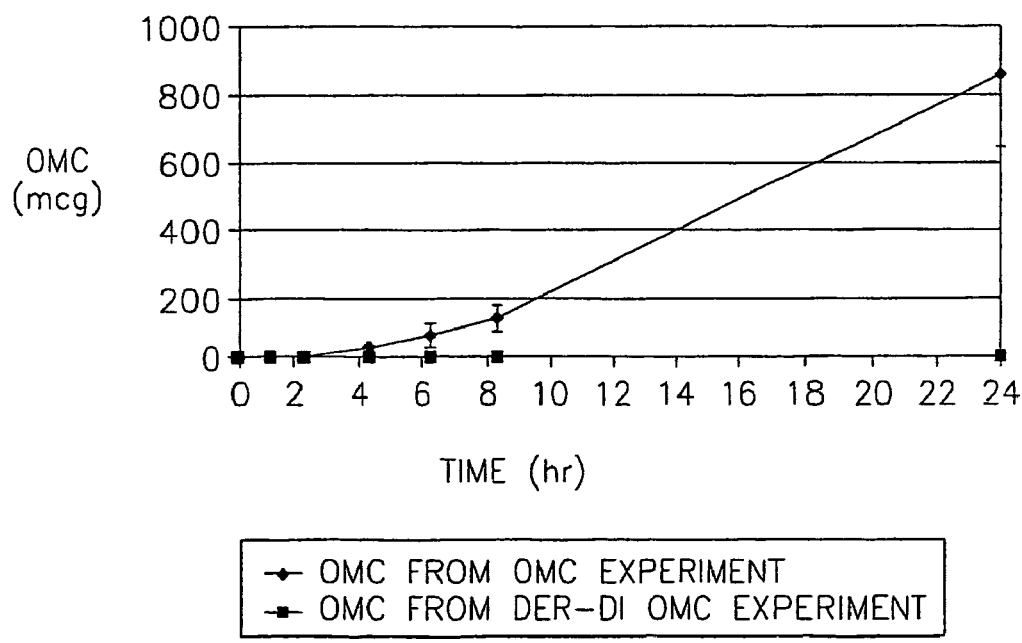
FIG. 6 presents the permeation profiles of OMC and di(4-methoxy cinnamoyl)jojobadiol through the skin.
Figure 7:
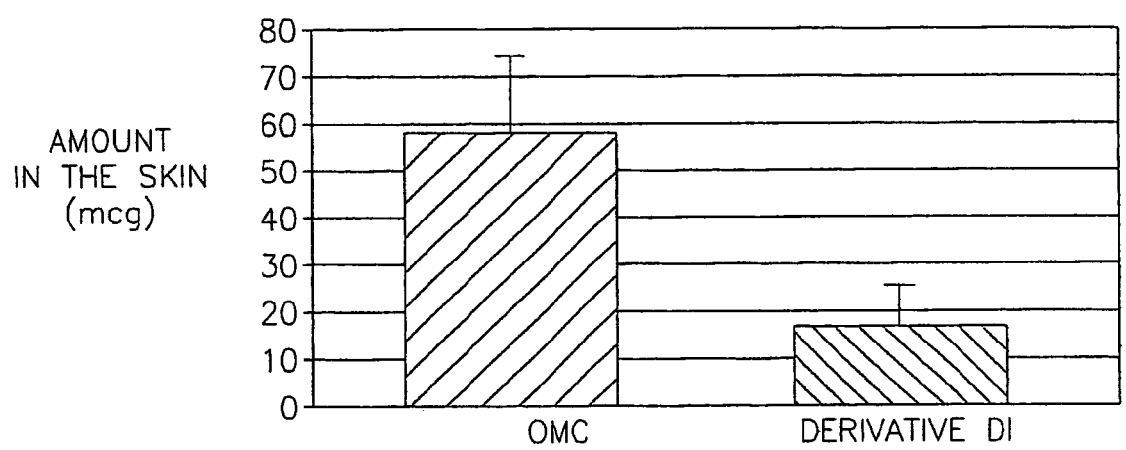
FIG. 7 presents the accumulation profiles in the skin of OMC and di(4-methoxy cinnamoyl)jojobadiol.

As is shown in the Example section, the above esterified compounds were shown to reduce skin permeability. Thus, the compound of the invention prevent or impedes permeation of small molecules through the skin. The term "penetrate" or "permeation" refers hereinabove, to introduction of the molecule into the skin layer where permeation refers to the process of transfer of the molecule and its absorption in the systemic system. FIG. 6 shows that OMC permeates to the skin while derivate di(4-methoxy-cinnamoyl)jojobadiol does not. FIG. 7 clearly show that OMC accumulates in higher amounts in the skin the amount of the di(4-methoxy-cinnamoyl)jojobadiol accumulate in the skin is about third of the amount of the OMC.

In addition, following immersion in water, it was shown that the amounts of di(4-methoxy-cinnamoyl)jojobadiol and tetra(4-methoxycinnamoyl)jojobatetraol on the skin following immersion in water were much higher than the amount of the OMC (see example 3 and 4). Therefore, the compound of the invention is also water resistant.

In another embodiment, one may use a method of oxymercuration for double bond monohydroxylation and osmium tetroxide catalyzed-$H_2O_2$ peroxidation with subsequent acidic hydrolysis for dihydroxylation of the Jojoba wax/oil ethylenic bonds. Treatment of the so obtained jojobadiol and jojobatetraol with p-methoxy-cinnamoyl chloride and pyridine yielded the corresponding esters, di(4-methoxy-cinnamoyl)jojobadiol (DMJD) and tetra(4-methoxycinnamoyl) jojobatetraol (TMJT) which were shown to be efficient UV-filteres. This method was shown to have three main advantages: (1) The reactions do not affect the Jojoba wax/oil ester group; (2) they give the hydroxylated end products in high yields and (3) the entire conversion of the wax/oil into di- or tetraols can be performed as a 'one pot' process, i.e. without isolation and purification of intermediates. When applied to the skin, formulations containing these esters proved to be several times more water-resistant than the most commonly used octylmethoxycinnamate.

In another embodiment the natural jojoba wax/oil is converted into jojobatetraol (see formula II, X=H) by osmiumtetroxice-catalyzed peroxydation of the cis-ethylenic bonds and subsequent acid hydrolysis under controlled conditions.

In another embodiment the jojobadiol (formula I, X=OH) and jojobatetraol (formula II, X=OH) are esterified with N- and O-protected aromatic aminoacids N-t-Boc-tryptophane and N-t.-Boc-O-benzyltyrosine, with subsequent elimination of the protecting group to yield the corresponding esters containing two or four aminoacid residues linked to the jojoba was backbone.

In another embodiment the jojobadiol (formula I, X=OH) and jojobatetraol (formula II, X=OH) are esterified with precursors of melanin, such as carboxylated derivatives of dopachrome red or O-protected leukodopachrome, to yield the corresponding esters containing two or four residues of the aforesaid melanin precursors linked to the jojoba wax/oil backbone.

In a similar way esterification of jojobadiol and jojobatetraol with protected aromatic aminoacids tryptophane and tyrosine (N-t.-Boc-tryptophane and Nn-t.-Boc-O-benzyltyrosine) and subsequent removal of the protecting t.-Boc-groups results in formation of the corresponding aminoacid esters bearing respectively two or four tryptophanes or tyrosines linked to the jojoba wax/oil backbone. An additional important advantage of the photoprotective jojoba wax/oil derivatives of tryptophan and tyrosine is the besides serving as UV-filters these aminoacid residues display also photocytoprotecting activity. Moreover, tyrosine is the precursor of melanin, a natural photoprotective and tanning agent.

Examples for estrifying agents are without being limited, UVA, UVB, UVA+UVB absorbers: Benzophenon-4 (2-hydroxy-4 methoxybenzophenone 5 sulphonic acid), Aminoanthraquinone-2-carboxylic acid, Para-amino-benzoic acid, Aminopterin, Anisylbenzoic acid, Aristolochic Acid (natuaal or synthetic).

Other examples are: Alminoprofen, Amfenac, p-Aminohippuric acid, p-Aminosalicylic acid, p-Anisic acid, o-(p-Anisoyl)benzoic acid, Aspartame, Aspirin, Caffeic acid, 9-Carbazoleacitic acid, Carprofen, Cinoxacin, Citrodisalyl, Clobuzarit, Clofibric acid, Clopirac, Diphenesenic acid, Ethacrynic acid, Fenclorac, Fenoprofen, Flurbiprofen, N-(p-Hydroxyphenyl)glycine, Indoleacitic acid, Lobenzarit, Menbuton, 3-(o-Methoxyphenyl)-2-phenylacrylic acid, Naproxen, Nicotinic acid, Oxiniacinic acid, Phenolphtalein sodium, Phenolphtalin, N-Phenylanthranilic acid, A-Phenylcinnamic acid, Phthalylsulfacetamide, Phthalylsulfathiazole, Phytochlorin, Piperic acid, Pranoprofen, 8-Quinolinecarboxylic acid, Rosoxacin, Salicylic acid, Salsalate, O-Thymotic acid, 2-(p-Toluyl)benzoic acid.

In another embodiment, the present invention provides a photoprotective or suntanning composition, comprises a compound comprising of hydroxylated derivatives of natural Jojoba wax/oil or its synthetic substitute, esterified with carboxylic acids or aminoacids bearing UV-absorbing groups and one or more further components selected from the group consisting of further emollients, skin moisturisers, skin tanning accelerators, antioxidants, emulsion stabilisers, thickening agents, moisture retention agents, film formers, preservatives, perfumes and colorants.

In another embodiment the composition may contain an oil phase which may comprise any oil conventionally used in cosmetic formulations, especially an emollient e.g., one or more of a fatty alcohol; hydrocarbon oil; a natural or synthetic triglyceride; a wax/oil including esters of long-chain acids and alcohols as well as compounds having wax/oil-like properties; a silicone oil; a fatty acid ester or a fatty alcohol; and lanoline-containing products.

Examples of fatty alcohols include cetyl alcohol, stearyl alcohol, octyldodecanol, cetearyl alcohol and oleyl alcohol; examples of hydrocarbon oils are, e.g., mineral oil (light or heavy), petrolatum (yellow or white), polyethylene, paraffin, squalane, microcrystalline wax/oil, ceresin, polybutene and hydrogenated polyisobutene; examples of a natural or synthetic triglyceride include castor oil, caprylic/capric triglyceride, Japan wax, hydrogenated vegetable oil, sweet almond oil, wheat germ oil, sesame oil, hydrogenated cottonseed oil, coconut oil, wheat germ glycerides, avocado oil, corn oil, trilaurin, hydrogenated castor oil, shea butter, cocoa butter, soybean oil, mink oil, sunflower oil, safflower oil, macadamia nut oil, olive oil, hydrogenated tallow, apricot kernel oil, hazelnut oil and borage oil; examples of a wax including esters of long-chain acids and alcohols as well as compounds having wax-like properties are, e.g., carnauba wax, beeswax (white or yellow), lanolin, candelellila wax, ozokerite, lanolin oil, paraffin, Japan wax, microcrystalline wax, ceresin, jojoba oil, cetyl esters wax, synthetic jojoba oil, synthetic beeswax and lanolin wax; a silicone oil is e.g. dimethicone or cyclomethicone; examples of a fatty acid ester or a fatty alcohol include isopropyl myristate, isopropyl palmitate, octyl palmitate, isopropyl lanolate, acetylated lanolin alcohol, the benzoate of C12-C15 alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate and isopropyl isostearate; and examples of lanoline-containing products include lanolin, lanolin oil, isopropyl lanolate, acetylated lanolin alcohol, acetylated lanolin, hydroxylated lanolin, hydrogenated lanolin and lanolin wax.

The emulsifier may comprise any emulsifier conventionally used in cosmetic formulations, e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester; an ethoxylated fatty acid; or an ethoxylated glyceride.

The composition of the invention may also comprise further components which are known to perform a useful function in a sunscreen composition. Examples of such further components include, e.g., emollients, skin moisturizers, skin tanning accelerators, antioxidants, emulsion stabilizers, thickening agents such as xanthan, moisture-retention agents such as glycerin, film formers, preservatives, perfumes and colorants.

The compound of the invention of the invention as defined by the general formula (I) and (II) may be formulated into any cosmetic preparations that are especially designed to be water-resistant. The total level of compound of the invention in these preparations will typically be on the order of about 0.5 to 60%, by weight, and in another embodiment within the range of about 5-30%, by weight. It is contemplated that the agents of this invention will be incorporated into formulations that are both effective and safe. An effective amount (or photoprotective amount) is that amount which is sufficient to significantly induce a positive effect of protection against UV sunlight as compared to a control. A safe amount is that which does not produce serious side effects.

The composition can be in the form of oily solutions, stick, lotions, creams, suspensions, spray aerosols, films, microcapsules, microspheres, liposomes, vesicles, emulsions, microemulsions, lipospheres, patches, solutions, ethosomes, ethanolic solutions, alcoholic solutions. The base of the formulation may be a water-in-oil emulsion, an oil-in-water emulsion, an oil-in-oil alcohol lotion, a vesicular dispersion, or as an emulsifier-free starch/lipid dispersions as described in U.S. Pat. Nos. 5,676,994 and 5,882,713, both herein incorporated by reference. The term "oil" is used herein to be inclusive of all lipids. The term "lipid" (or fat) is a comprehensive term referring to substances which are found in living cells and which are comprised of only a nonpolar hydrocarbon moiety or a hydrocarbon moiety with polar functional groups (see the Encyclopedia of Chemistry, 3rd Edition, C. A. Hampel and G. G. Hawley, eds., 1973, p. 632, herein incorporated by reference). Most lipids are insoluble in water and are soluble in fat solvents such as ether and chloroform.

Other components that may be included in the sunscreen formulations of the invention include: other UVA and UVB sunscreen agents, such as 2-phenyl-benzimidazole-5-sulfonic acid, TEA salicylate, octyl dimethyl PABA, padimate-O (2-ethylhexyl 4-(dimethylamino) benzoate) and octyl methyl cinnamate; inorganic physical sunblocks, such as zinc oxide and TiO.sub.2; artificial tanning agents; abrasives; absorbents: fragrances; pigments; colorings/colorants; essential oils; skin sensates; astringents carriers and vehicles; thickening/structuring agents; emollients; emulsion stabilizers; excipients and auxiliaries commonly incorporated into cosmetic formulations; humectants; moisturizers; skin conditioners; anti-caking agents; antifoaming agents; antimicrobial agents; antioxidants; binders; buffering agents; bulking agents; chelating agents; chemical additives; film formers; humectants; opacifying agents; skin-conditioning agents; vitamins; and the like.

As previously indicated, the compositions of the invention are useful as sunscreen agents to provide protection from adverse effects of UV radiation. The principal application is as a topical sunburn protectant for human skin. However, it is envisioned that the compositions and formulations of the invention would also have veterinary applications as a skin protectant. The sunscreen formulations contemplated herein may be applied to the skin by spreading or spraying a thin layer thereof over the skin surface intended to be protected.

Resins, when used, include, but are not limited to, aromatic/aliphatic resins, hydrogenated aromatic resins, polyterpene, synthetic resins (including pentaerythrityl hydrogenated rosinate), rosin, acrylics, silicones, and other resins (including polyol prepolymers and LEXOREZ 100 resins, sold by Inolex Corporation).

Gellants include, but are not limited to, clays (including stearalkonium hectorite, quaternium-18 bentonite, and quaternium-18 hectorite), and metal soaps (including aluminum and zinc stearates).

Colorants and pearls preferably include a classic raw material without any surface treatment. Fillers include, but are not limited to, mica, talc, and sericite. Functional fillers include, but are not limited to, spherical particles (including PMMA, silica, nylon, and microbubbles), boron nitride, starches, silica, lauroyl lysine, and teflon. Wetting agents include, but are not limited to, low HLB emulsifiers, polyglyceryl esters (including polyglyceryl-3 diisostearate), hydrogentated lecithin, lanolin alcohols, polyhydroxystearic acid, and soya sterols.

Texturizing agents in an anhydrous foundation of the invention preferably are surface treated. Texturizing agents include, but are not limited to, nylon, PMMA, serecite, talc, mica, boron nitride, teflon, microbubbles (including glass and polyvinylidene), spherical silica, starches (including oat, rice, wheat, and corn), bismuth oxychloride, microcrystalline cellulose, polyurethane powder, and silicone powder.

Pigments preferably are surface treated and include, but are not limited to, titanium dioxide (including pigmentary and ultrafine), zinc oxide (including pigmentary and ultrafine), and iron oxides (including pigmentary and ultrafine).

Surface treated raw materials are preferred in these embodiments to improve dispersibility and enhance solids loading to provide a a drier texture, create a matte appearance, and improve wear.

Another aspect of the invention is to provide cosmetic compositions, including pressed face powder, loose face powder, pressed face foundation, blush, eyeshadow, anhydrous foundation, anhydrous mascara, anhydrous eyeshadow, glossy classic lipstick, matte classic lipstick, and volatile lipstick, that generally include about 0.01 wt. % to about 20 wt. % of a compound of formula (I) or (II).

In another embodiment the compound of the invention can be used in preparation for the treatment of skin conditions selected from the group consisting of acne, psoriasis, seborrheic dermatitis, dandruff, warts, corns, calluses, ringworm infection, wrinkling, yellowing, leatheriness, mottling, and hyperpigmentation. The presence of the compound of the invention will prevent the permeation of the compositions for treating these conditions into deeper layers of the skin, and will prevent their wash by water. When used as a treatment for skin conditions, a compound of formula (I) preferably will be delivered in a safe and effective amount. The term "safe and effective amount" is defined as any amount sufficient to induce a positive modification in the condition to be treated, but low enough to avoid serious side effects (at a reasonable benefit/risk ratio), within the scope of sound medical, judgement. The safe and effective amount of the compounds of formula (I) will vary with the particular condition being treated, the age and physical condition of the patient being treated, the severity of the condition, the duration of the treatment, the nature of concurrent therapy, the specific compound or compounds of the invention being employed, the particular carrier used, if any, and similar factors in the knowledge and expertise of the attending physician.

EXAMPLES

Example 1

Preparation of Di(4-methoxycinnamoyl)jojobadiol

A solution of 12.12 g Jojoba wax/oil (appr. 0.02 mol) in 80 mL tetrahydrofuran is added to 12.74 g (0.04 mol) mercury acetate in 20 mL water and 0.1 mL acetic acid, and the mixture is stirred for 6.5 h in closed vessel in an atmosphere of nitrogen, the course of the reaction being followed by TLC. Thereafter, sodium borohydride (0.7 g) in 40 mL 1.5 M NaOH is added in small portions with constant stirring so that the temperature of the reaction mixture never exceeds 30° C., and stirring is continued for 2 h. After setting down of the mercury the aqueous layer is saturated with NaCl, the layers are separated and tetrahydrofuran is removed from the upper layer by distillation. The residue is dissolved in 60 mL chloroform and washed three times with 40 mL of saturated sodium chloride solution and dried over anhydrous sodium sulfate. The oily jojobadiol 10.86 g (84.6%) solidifies upon standing at room temperature to form colorless crystals of the erythro isomer, m. p. 86-88 C. IR (neat): 3300-3400, 1750 cm $^1$H NMR: 4.8-4.9 (2H, OH, bs), 3.96-4.00 (triplet, —$CH_2$OCO), 3.6 92H, CHOH), 2.20-2.26 (triplet, $CH_2$COO), 1.2-1.4 (aliphatic hydrogens), 0.92-0.94 (triplet, $CH_3$).

A solution of 4.0 g (appr. 6.2 mmol) of jojobadiol (mixture of threo- and erythro forms) in 60 mL chloroform containing 1 g (13 mmol) pyridine is added dropwise under constant stirring at room temperature to a solution of 2.48 g (13 mmol) of 4-methoxycinnamoyl chloride in 40 mL chloroform. Stirring is continued for 1 h, the mixture is washed consecutively with water, diluted HCl, water, 10% aqueous NaOH, water and dried over anhydrous sodium sulfate. The solution is concentrated and the residue is purified by column chromatography over Silica gel 60 using as eluent a mixture of diethyl ether—petroleum ether (1:9, v/v). Di(4-methoxycinnamoyl)jojobadiol is obtained as a colorless viscous liquid. Yield 3.1 g (48.4%). IR: 1725, 1620, 1602, 1580, 1520 cm 1H NMR: 7.7 (2H, CH=CH, d), 7.47-7.50 (4H, $C_6H_4$), 6.3 (2H, CH=CH), 3096-4.00 (triplet, —$CH_2$OCO), 3.80 (6H, $OCH_3$, s), 3.76 (2H, CHOCO, m), 2.16 (triplet, —$CH_2$COO), 1.2-1.4, aliphatic hydrogens). UV: max 290 nm.

Example 2

Preparation of Tetra (4-methoxycinnamoyl)jojobatetraol

Osmium tetroxide (1 g) is dissolved in 200 mL diethyl ether. 1 mL of that solution is added to a solution of 12.12 g (appr. 0.02 mol) Jojoba wax/oil in 20 mL acetone and 40 mL diethyl ether. To the latter solution 6 mL of 30% hydrogen peroxide is added dropwise under constant stirring so that the reaction temperature never exceeds 30° C. The mixture is stirred for 8 h at room temperature and concentrated in vacuum. The residual viscous oil is dissolved in 40 mL petroleum ether and boiled gently with 40 mL 20% hydrochloric acid. The course of the reaction is followed by TLC. After boiling for 4.5 h the mixture is cooled to room temperature, the layers are separated, the upper layer is washed three times with 40 mL of saturated NaCl and then dried over anhydrous sodium sulfate. Evaporation under reduced pressure gives 10, 5 g (yield 78.1%) of jojobatetraol as a very viscous colorless oil comprising a mixture of erythro- (main component) and threo-isomers. IR (neat): broad singlets at 3300-3400, 1700 cm. The $^1$H NMR spectrum showed signals in the 3.75 (4H, —CHOH, m) and 3.45 (H, —CHOH) regions corresponding respectively to the erythro- and threo-forms in a ratio of appr. 4:1.

Esterification of jojoba tetraol (4 g, 5.9 mmol) with 4.64 g (23.6 mmol) p-methoxycinnamoyl chloride and 2 g pyridine was performed under the conditions described above for the diol. Tetra (4-methoxycinnamoyl)jojobatetraol (yield 94.4%) was obtained as a slightly yellow viscous liquid. UV: max 291 nm; 1 g 5.02 (calculated for the averaged MW). The $^1$H NMR spectrum coincided with that of the dimethoxycinnamoyl ester of jojobadiol shown above differing by a higher integral intensity of the corresponding proton signals.

Example 3

Substantivity of Di(4-methoxycinnamoyl)jojobadiol

The objective of the experiment was to compare the substantivity of derivative DI of OMC vs. OMC (the term "OMC" refers hereinabove to octylmethoxycinnamate. An experiment was conducted by applying a formulation containing the new derivative to the skin of nude mice and then the skin was immersed in water and dried consecutively 2 times. The immersion time was for 20 minutes each time and the drying period was 15 minutes. A formulation containing OMC was used as control.

Formulations:

1. Formula Di(4-methoxycinnamoyl)jojobadiol (DI): (5% der DI)

|  | g |
| --- | --- |
| propylene glycol | 2.5 |
| ethanol | 2.5 |
| brij 52 | 0.3 |
| Di(4-methoxycinnamoyl)jojobadiol | 0.5 |
| water | 4.2 |

2. Formula OMC: (5% OMC)

|  | g |
| --- | --- |
| propylene glycol | 2.5 |
| ethanol | 2.5 |
| brij 52 | 0.3 |
| OMC | 0.5 |
| water | 4.2 |

3. Pure OMC

The conditions used were as follows:

| Skin: | frozen from nude mice 7-9 weeks, male |
| --- | --- |
| t° C.: | room temperature |
| Solvent medium: | distillated water |
| Quantity of formula on skin: | 5 mg |
| Surface of skin: | 6.4 mm$^2$ |
| Skin extracts: | 10 ml of EtOH |

Experimental Results

The amount of the derivatives remained on the skin after this operation is provided in FIG. 1.

It can be clearly seen that the amount of the Di(4-methoxycinnamoyl)jojobadiol which was remained on the skin after was much higher (about 80%) than the amount of OMC remained on the skin which was about 50%.

Example 4

Substantivity of Tetra (4-metoxycinnamoyl)jojobatetraol (TETRA)

The objective of the experiment was to compare the substantivity of derivative TETRA of OMC vs. OMC. An experiment was conducted by applying a formulation containing the new derivative to the skin of nude mice and then the skin was immersed in water and dried consecutively 2 times. The immersion time was for 20 minutes each time and the drying period was 15 minutes. A formulation containing OMC was used as control.

Formulations:

2. Formula Tetra (4-metoxycinnamoyl)jojobatetraol: (5% TETRA)

|  | g |
| --- | --- |
| propylene glycol | 2.5 |
| ethanol | 2.5 |
| brij 52 | 0.3 |
| Tetra (4-metoxycinnamoyl)jojobatetraol | 0.5 |
| water | 4.2 |

2. Formula OMC: (5% OMC)

|  | g |
| --- | --- |
| propylene glycol | 2.5 |
| ethanol | 2.5 |
| brij 52 | 0.3 |
| OMC | 0.5 |
| water | 4.2 |

3. Pure OMC

The conditions used were as follows:

| Skin: | frozen from nude mice 7-9 weeks, male |
| --- | --- |
| t° C.: | room temperature |
| Solvent medium: | distillated water |
| Quantity of formula on skin: | 5 mg |
| Surface of skin: | 6.4 mm$^2$ |
| Skin extracts: | 10 ml of EtOH |

Experimental Results

The amount of the derivatives remained on the skin after the immersion in water and drying is provided in FIG. 1.

It can be clearly seen that the amount of the Tetra (4-metoxycinnamoyl)jojobatetraol which was remained on the skin after was much higher (about 90%) than the amount of OMC remained on the skin which was about 30%.

Example 5

Measurement of Skin Permeation of Di(4-methoxycinnamoyl)jojobadiol in Comparison to OMC The permeation of pure OMC and Di(4-methoxycinnamoyl)jojobadiol (two —OH groups esterified) was measured by using dorsal skin of male, 7 weeks old, nude mice (CD1, Weizmann Institute, Israel).

The experiments were carried out for 24 hours at 37° C. in Franz diffusion cells. Samples of 200 µl were taken at 1, 2, 4, 6, 8 and 24 hours. 10 mg of each compound were applied on each skin (area—1.77 cm$^2$). The receiver compartment contained EtOH:H$_2$O (1:1). At the end of the experiment the skin was cleaned and the skins were extracted with 10 ml EtOH. The amounts of the OMC and derivative Di(4-methoxycinnamoyl)jojobadiol were assayed by HPLC.

Determination of OMC and Derivative Di(4-methoxycinnamoyl)jojobadiol by HPLC

HPLC Equipment:

Merck-Hitachi D-7000 Interface

Merck-Hitachi C-7400 variable UV detector

Merck-Hitachi L-7300 column oven

Merck-Hitachi L-7200 auto-sampler

Merck-Hitachi L-7100 pump

Merck-Hitachi HSM computerized analysis program.

HPLC Conditions:

OMC:

Mobile Phase: 12% DDW+88% Methanol

Flow: 1.5 ml/min

Temperature: 35° C.

UV detection wave: 308 nm

Column: LiChrospher 100, RP-18, 5μ, 250×4 mm (LiChro-CART)

Injection volume: 50 μl

Figure 3:
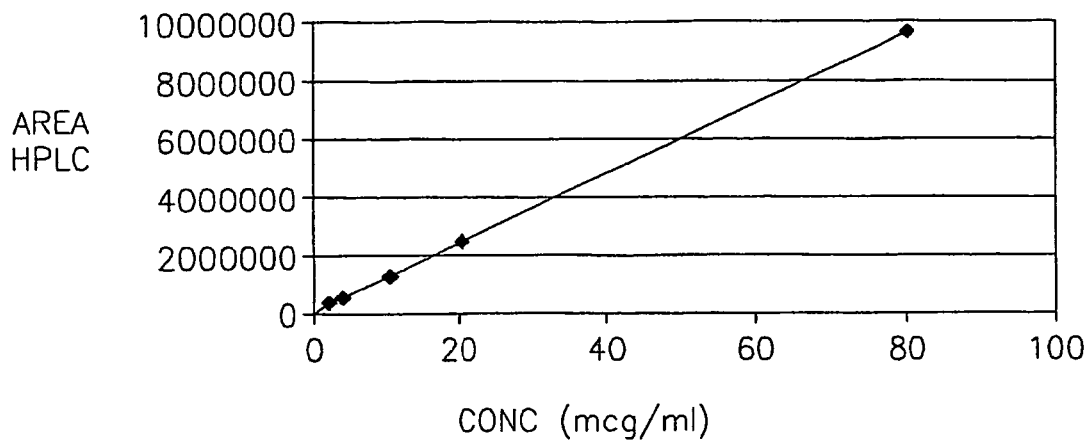
FIG. 3 presents OMC (octylmethoxycinnamate) standard curve as detected by HPLC method for OMC.

FIG. 3 demonstrates the OMC standard curve as detected by HPLC method for OMC

Derivative Di:

Mobile Phase: 100% Methanol

Flow: 1.5 ml/min

Temperature: 35° C.

UV detection wave: 308 nm

Column: LiChrospher 100, RP-18, 5μ, 250×4 mm (LiChro-CART)

Injection volume: 50 μl

Minimum detected amount of Di(4-methoxycinnamoyl)jojobadiol is 800 ng/ml

Figure 4:
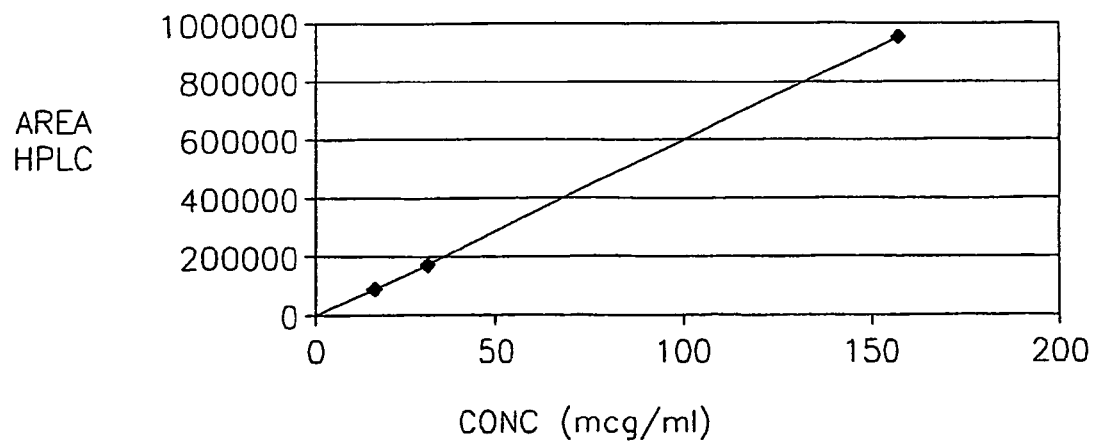
FIG. 4 presents di(4-methoxy cinnamoyl)jojobadiol standard curve as detected by HPLC method for di(4-methoxy cinnamoyl)jojobadiol.
Figure 5:
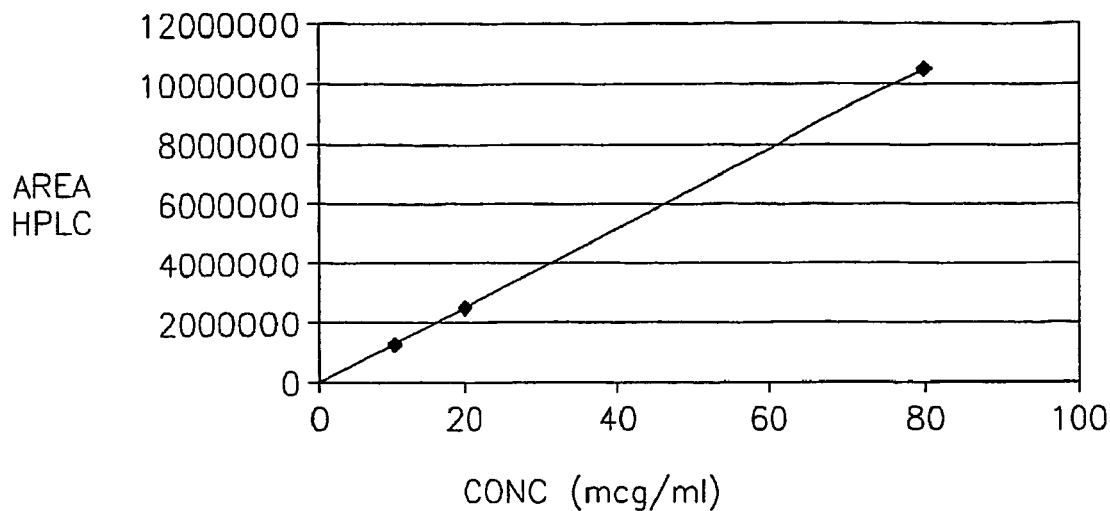
FIG. 5 presents OMC (Octyl Methoxy Cinnemate) standard curve as detected by di(4-methoxy cinnamoyl)jojobadiol HPLC method.

Standard curves for derivative Di(4-methoxycinnamoyl) jojobadiol and OMC as measured by derivative Di HPLC method are presented in FIGS. 4 and 5.

EXPERIMENTAL RESULTS

The results of permeation of OMC from OMC and derivative Di(4-methoxycinnamoyl)jojobadiol permeation experiments are summarized in FIG. 6. The amount of OMC which penetrated into the skin at the end of OMC permeation experiment was 876±235 μg. This amount represents 8.76% of the dose applied on the skin.

In contrast, no penetration of derivative Di(4-methoxycinnamoyl)jojobadiol across the skin was observed throughout 24 hours in vitro permeation experiment (the lowest detectable concentration of the derivative Di(4-methoxycinnamoyl)jojobadiol by HPLC assay was 0.8 μg/ml).

The amounts of OMC and derivative Di(4-methoxycinnamoyl)jojobadiol accumulated in the skin at the end of experiment are presented in FIG. 7. It can be clearly seen that OMC skin accumulation was three times higher than that of derivative Di (2956±807 and 900±359 μg, respectively).

In Conclusion:

The above experimental results indicate that while OMC permeates and penetrates the model skin in relatively high amounts, Di(4-methoxycinnamoyl)jojobadiol derivative impedes this penetration.

What is claimed is:

1. A photoprotective composition for topical application comprising a hydroxylated derivative of natural or synthetic Jojoba wax/oil, wherein one or more of the hydroxyl groups of the hydroxylated derivative are esterified with a UV-absorbing moiety selected from the group consisting of a UV-absorbing carboxylic acid and a UV-absorbing amino acid.

2. The photoprotective composition according to claim 1, wherein the esterified hydroxylated derivative does not permeate through the skin.

3. The photoprotective composition of claim 1, wherein the composition is water resistant.

4. The photoprotective composition according to claim 1, wherein the composition inhibits penetration of small molecules through the skin.

5. The photoprotective composition according to claim 1, wherein the UV absorbing moiety is selected from the group consisting of UVA absorbers, UVB absorbers and UVA and UVB absorbers.

6. The photoprotective composition according to claim 1, wherein the hydroxylated derivative of natural or synthetic Jojoba wax/oil being esterified is a diol or a tetraol of natural or synthetic Jojoba wax/oil.

7. The photoprotective composition according to claim 6, wherein the esterified hydroxylated derivative is an esterified diol of the general formula (I):

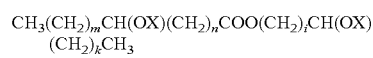

wherein
each of m, n, i and k, independently of each other, is an integer from 5 to 30 and each of X, independently, is a UV-absorbing organic moiety.

8. The photoprotective composition according to claim 6, wherein the esterified hydroxylated derivative is an esterified tetraol of the general formula (II):

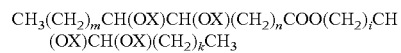

wherein
each of m, n, i and k, independently of each other, is an integer from 5 to 30 and each of X, independently, is a UV-absorbing organic moiety.

9. The photoprotective composition according to claims 7 and 8, wherein the UV-absorbing organic moiety is selected from the group consisting of 4-methoxycinnamate, tryptophanate, benzyltyrosinate, aminoanthraquinone-2-carboxylate, 4-aminobenzoate, anisylbenzoate, aristolochate, aminopterin, 4-aminohippurate, 4-aminosalicylate, 2-(4-anisoyl)benzoate, hydroxysalicylate, salicylate, caffeate, 9-carbazoleacetate, ethacrynate, 3-(2-methoxyphenyl)-2-phenylacrylate, nicotinate, oxiniacinate, N-phenylanthranilate, alpha-phenylcinnamate, piperate, 8-quinolinecarboxylate, O-thymotate, benzophenone-4-(2-hydroxy-4-methoxy benzophenone-5-sulphonate) and 2-(p-tolyl) benzoate.

10. The photoprotective composition according to claim 9, wherein the UV-absorbing moiety is 4-methoxycinnamate.

11. The photoprotective composition according to claim 7, wherein the esterified diol is di-(4-methoxycinnamoyl)jojobadiol.

12. The photoprotective composition according to claim 8, wherein the esterified tetraol is tetra-(4-methoxycinnamoyl) jojobatetraol.

13. The photoprotective composition according to claim 1, further comprising one or more component selected from the group consisting of an emollient, a skin moistener, a skin tanning accelerator, an antioxidant, an emulsion stabilizer, a thickening agent, a moisture retention agent, a film former, a preservative and a colorant.

14. The photoprotective composition according to claim 1, wherein the composition is in a form selected from the group consisting of an oily solution, a lotion, a cream, a suspension, a spray aerosol, a film, a microcapsule, a microsphere, a liposome, a vesicle, an emulsion, a microemulsion, a liposphere, a patch, a solution, an ethosome, an ethanolic solution and an alcoholic solution.

15. A hydroxylated derivative of natural or synthetic Jojoba wax/oil, wherein one or more of the hydroxyl groups of the hydroxylated derivative is esterified by a UV-absorbing moiety selected from the group consisting of a UV-absorbing carboxylic acid and a UV-absorbing amino acid.

16. The derivative according to claim 15, being a diol or a tetraol of natural or synthetic Jojoba wax/oil.

17. The derivative according to claim 16, being an esterified diol of the general formula (I):

$$CH_3(CH_2)_m CH(OX)(CH_2)_n COO(CH_2)_i CH(OX)(CH_2)_k CH_3$$

wherein
each of m, n, i and k, independently of each other, is an integer from 5 to 30 and each of X, independently, is a UV-absorbing organic moiety.

18. The derivative according to claim 16, being an esterified tetraol of the general formula (II):

$$CH_3(CH_2)_m CH(OX)CH(OX)(CH_2)_n COO(CH_2)_i CH(OX)CH(OX)(CH_2)_k CH_3$$

wherein
each of m, n, i and k, independently of each other, is an integer from 5 to 30 and each of X, independently, is a UV-absorbing organic moiety.

19. The derivative according to claims 17 and 18, wherein the UV-absorbing organic moiety is selected from the group consisting of 4-methoxycinnamate, tryptophanate, benzyltyrosinate, aminoanthraquinone-2-carboxylate, 4-aminobenzoate, anisyl benzoate, aristolochate, aminopterin, 4-aminohippurate, 4-aminosalicilate, 2-(4-anisoyl)benzoate, hydroxysalicilate, salicilate, caffeate, 9-carbazoleacetate, ethacrynate, 3-(2-methoxyphenyl)-2-phenylacrylate, nicotinate, oxiniacinate, N-phenylanthranilate, alpha-phenylcinnamate, piperate, 8-quinolinecarboxylate, O-thymotate, benzophenone-4-(2-hydroxy-4-methoxy benzophenone-5-sulphonate) and 2-(p-tolyl)benzoate.

20. The derivative according to claim 19, wherein the UV-absorbing moiety is 4-methoxycinnamate.

21. The derivative according to claim 17, wherein the derivative is di-(4-methoxycinnamoyl)jojobadiol.

22. The derivative according to claim 18, wherein the derivative tetra-(4-methoxycinnamoyl)jojobatetraol.

23. A composition, comprising
an esterified tetraol of the general formula (II):

$$CH_3(CH_2)_m CH(OX)CH(OX)(CH_2)_n COO(CH_2)_i CH(OX)CH(OX)(CH_2)_k CH_3$$

wherein each of m, n, i and k, independently of each other, is an integer from 5 to 30, and each X, independently, is a UV-absorbing organic moiety.

24. An esterified tetraol of the general formula (II):

$$CH_3(CH_2)_m CH(OX)CH(OX)(CH_2)_n COO(CH_2)_i CH(OX)CH(OX)(CH_2)_k CH_3,$$

wherein each of m, n, i and k, independently of each other, is an integer from 5 to 30, and each X, independently, is a UV-absorbing organic moiety.

* * * * *

UNITED STATES PATENT AND TRADEMARK OFFICE
CERTIFICATE OF CORRECTION

PATENT NO. : 7,736,630 B2 Page 1 of 1
APPLICATION NO. : 10/473358
DATED : June 15, 2010
INVENTOR(S) : Elka Touitou and Lev Bergelson It is certified that error appears in the above-identified patent and that said Letters Patent is hereby corrected as shown below:

On the Title Page
Please add in the following:

Item -- (60) Provisional application
No. 60/281,626, filed
on Mar. 30, 2001 --

Signed and Sealed this

Tenth Day of August, 2010

David J. Kappos
*Director of the United States Patent and Trademark Office*